US00PP15941P2

(12) United States Plant Patent
Noordhuis

(10) Patent No.: US PP15,941 P2
(45) Date of Patent: Sep. 6, 2005

(54) ***GERANIUM* PLANT NAMED 'NEW DIMENSION'**

(50) Latin Name: *Geranium pratense*
Varietal Denomination: New Dimension

(75) Inventor: Bart Noordhuis, Boyl (NL)

(73) Assignee: Compass Plant Group, Lisse (NL)

( * ) Notice: Subject to any disclaimer, the term of this patent is extended or adjusted under 35 U.S.C. 154(b) by 204 days.

(21) Appl. No.: 10/437,959

(22) Filed: May 13, 2003

(51) Int. Cl.[7] ..... A01H 5/00
(52) U.S. Cl. ..... Plt./324
(58) Field of Search ..... Plt./324

*Primary Examiner*—Kent Bell
(74) *Attorney, Agent, or Firm*—C. A. Whealy

(57) ABSTRACT

A distinct cultivar of *Geranium* plant named 'New Dimension', characterized by its upright, outwardly spreading and uniform plant habit; freely flowering habit; and light violet-colored flowers.

2 Drawing Sheets

Botanical classification/cultivar designation: *Geranium pratense* cultivar New Dimension.

BACKGROUND OF THE INVENTION

The present Invention relates to a new and distinct cultivar of *Geranium* plant, botanically known as *Geranium pratense*, and hereinafter referred to by the cultivar name New Dimension.

The new *Geranium* is a naturally-occurring whole plant mutation of the *Geranium pratense* cultivar Victor Reiter, not patented. The new *Geranium* was discovered by the Inventor in May, 1999 in a controlled environment in Vinhega, The Netherlands. The new *Geranium* was selected on the basis of its numerous uniquely colored flowers.

Asexual reproduction of the new cultivar by micropropagation in a laboratory in Zandvoort, The Netherlands has shown that the unique features of this new *Geranium* are stable and reproduced true to type in successive generations.

SUMMARY OF THE INVENTION

Plants of the cultivar New Dimension have not been observed under all possible environmental and cultural conditions. The phenotype may vary somewhat with variations in environment such as temperature and light intensity without, however, any variance in genotype.

The following traits have been repeatedly observed and are determined to be the unique characteristics of 'New Dimension'. These characteristics in combination distinguish 'New Dimension' as a new and distinct cultivar:

1. Upright, outwardly spreading and uniform plant habit.
2. Freely flowering habit.
3. Light violet-colored flowers.

Plants of the new *Geranium* are most similar to plants of the parent, the cultivar Victor Reiter, however plants of the new *Geranium* differ from plants of the cultivar Victor Reiter in the following characteristics:

1. Plants of the new *Geranium* are more uniform in plant shape than plants of the cultivar Victor Reiter.
2. Plants of the new *Geranium* are more freely flowering than plants of the cultivar Victor Reiter.
3. Plants of the new *Geranium* and the cultivar Victor Reiter differ in flower color.

BRIEF DESCRIPTION OF THE PHOTOGRAPHS

The accompanying colored photographs illustrate the overall appearance of the new *Geranium*, showing the colors as true as it is reasonably possible to obtain in colored reproductions of this type. Colors in the photographs may differ slightly from the color values cited in the detailed botanical description which accurately describe the colors of the new *Geranium*.

The photograph on the first sheet comprises a side perspective view of a typical one-year old flowering plant of 'New Dimension' grown in a container.

The photograph at the top of the second sheet is a close-up view of a typical open flower of 'New Dimension'.

The photograph at the bottom of the second sheet is a close-up view of the upper surface of a typical leaf of 'New Dimension'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and following description were about one year old and grown under outdoor field conditions which closely approximate commercial production conditions in Boskoop, The Netherlands. During the production of the plants, day temperatures ranged from 14 to 27° C. and night temperatures ranged from 4 to 16° C. The photographs and description were taken in July, 2002.

Botanical classification: *Geranium pratense* cultivar New Dimension.

Parentage: Naturally-occurring whole plant mutation of the *Geranium pratense* cultivar Victor Reiter, not patented.

Propagation:

*Type.*—By micropropagated plantlets.

*Time to initiate roots.*—About 40 days.

*Time to produce a rooted micropropagated plantlet.*—About 90 days.

*Root description.*—Thick; light brown in color.

Plant description:

*Form.*—Perennial flowering plant; upright, outwardly spreading, mounded and uniform growth habit; inverted triangle.

*Plant height.*—About 27 cm.

*Plant diameter.*—About 32 cm.

*Vigor.*—Moderately vigorous.

*Lateral branch description.*—Number per plant: Freely branching, about six lateral branches per plant. Length: About 9.1 cm. Diameter: About 4 mm. Internode length: About 9.1 cm. Strength: Strong. Texture, upper and lower surfaces: Densely pubescent. Fragrance: Aromatic when rubbed. Color: 178A to 183A.

*Stipule description.*—Quantity: Two stipules per internode. Length: About 9 mm. Width: About 3.5 mm. Shape: Lanceolate. Texture: Pubescent. Color: 185A.

*Foliage description.*—Arrangement: Opposite, simple. Length: About 8 cm. Width: About 7.6 cm. Shape: Deeply palmately lobed. Apex: Acute. Base: Hastate. Margin: Deeply incised. Texture, upper surface: Smooth, glabrous. Texture, lower surface: Dense pubescence at main veins and margins. Venation pattern: Palmate. Petiole: Length: About 13 cm. Diameter: About 2 mm. Color: Developing foliage, upper surface: Between 137A and 139A. Developing foliage, lower surface: 138A. Mature foliage, upper surface: 137A; apices, between N186A to 200A. Mature foliage, lower surface: 138A to 138B. Venation, upper surface: 137A. Venation, lower surface: 138B to 138C. Petiole, upper surface: 178A. Petiole, lower surface: 148A.

Flower description:

*Appearance.*—Single rotate flowers with five petals arranged on open cymes; flowers face mostly outwardly. Flowers not persistent.

*Quantity of flowers.*—Freely flowering habit, about 15 flowers per lateral stem.

*Natural flowering season.*—Plants flower continuously from June to mid-July in The Netherlands.

*Fragrance.*—None detected.

*Flower longevity on the plant.*—About five days.

*Inflorescence height.*—About 5.2 cm.

*Inflorescence diameter.*—About 7.6 cm.

*Flower diameter.*—About 3.6 cm.

*Flower height* (*depth*).—About 1.7 cm.

*Flower buds* (*about five days before opening*).—Length: About 1 cm. Diameter: About 5 mm. Shape: Ovoid. Color, upper surface: 200C. Color, lower surface: 138A.

*Petals.*—Quantity per flower: About five. Length: About 2 cm. Width: About 1.6 cm. Shape: Broadly obovate. Apex: Rounded, somewhat irregular. Base: Attenuate. Margin: Entire. Texture: Slightly ruffled; base of petals, glandular pubescence. Color: When opening, upper and lower surfaces: N88B; venation, 85C; venation less pronounced on lower surface. Fully opened, upper and lower surfaces: N87A to N87B; venation, 85D; venation less pronounced on lower surface.

*Sepals.*—Quantity per flower: Five. Length: About 9 mm. Diameter: About 6 mm. Calyx shape: Rotate; slightly cupped. Shape: Ovate. Apex: Aristate. Base: Cuneate. Margin: Entire. Texture, upper surface: Smooth. Texture, lower surface: Glandular pubescence. Color: Immature and mature, upper surface: 143B; longitudinal stripes, 165B. Immature and mature, lower surface: 165A; longitudinal stripes, 200C.

*Peduncles.*—Length: About 5.8 cm. Diameter: About 3 mm. Angle: About 30 to 50° from vertical. Strength: Strong. Color: 178A to 183A.

*Pedicels.*—Length: About 8 mm. Diameter: About 1.5 mm. Angle: About 30 to 50° from vertical. Strength: Strong. Color: 178A to 183A.

*Reproductive organs.*—Stamens: Quantity per flower: About ten. Anther shape: Oblong; dorsifixed. Anther size: About 1 mm by 2 mm. Anther color: N186A. Pollen amount: Scarce. Pollen color: 197A. Pistils: Quantity per flower: One. Pistil length: About 1 cm. Style length: About 8 mm. Style color: 174C; towards the base, 138A. Stigma color: 174B. Ovary color: 138A.

*Fruits.*—Quantity per flower: One. Length: About 3 cm. Diameter: About 3 mm. Texture: Smooth with longitudinal ridges. Color, upper surface: 177A. Color, lower surface: 138A.

*Seeds.*—Quantity per fruit: About 50. Length: About 1 mm. Diameter: About 1 mm. Color: 175A to slightly darker than 175A.

Disease/pest resistance: Plants of the new *Geranium* have not been noted to be resistant to pathogens and pests common to *Geranium.*

Temperature tolerance: Plants of the new *Geranium* have been observed to be tolerant to temperatures ranging from −20 to 40° C.

It is claimed:

1. A new and distinct cultivar of *Geranium* plant named 'New Dimension', as illustrated and described.

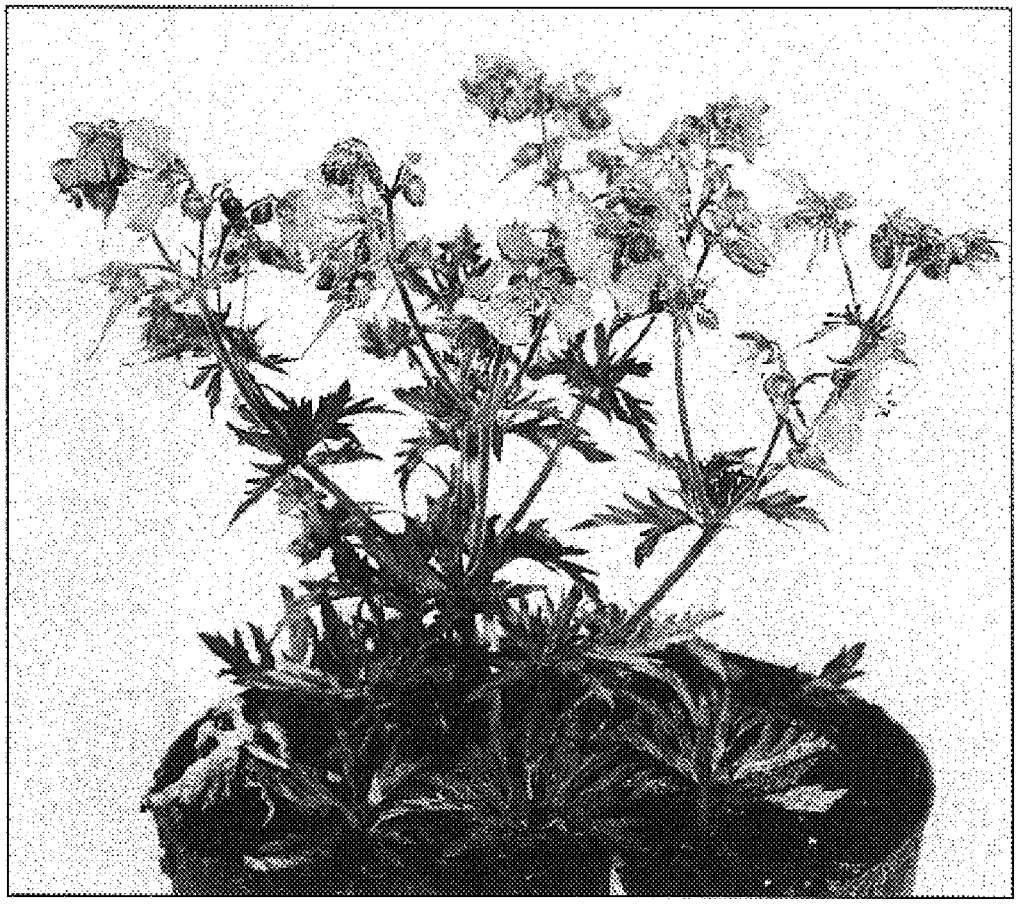

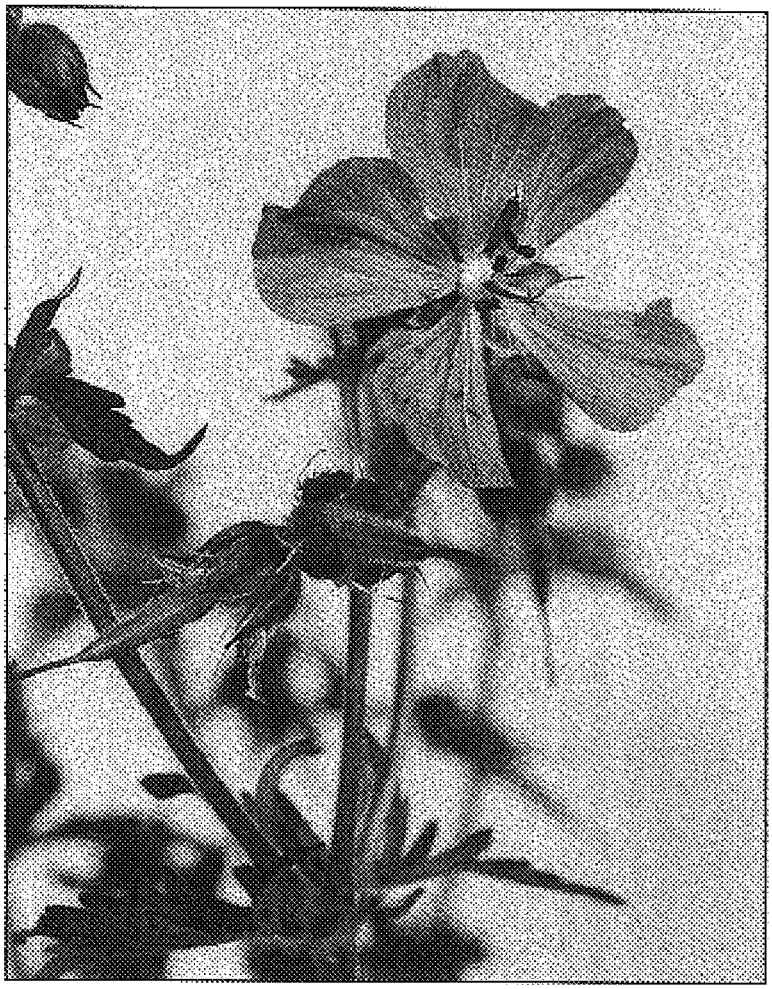
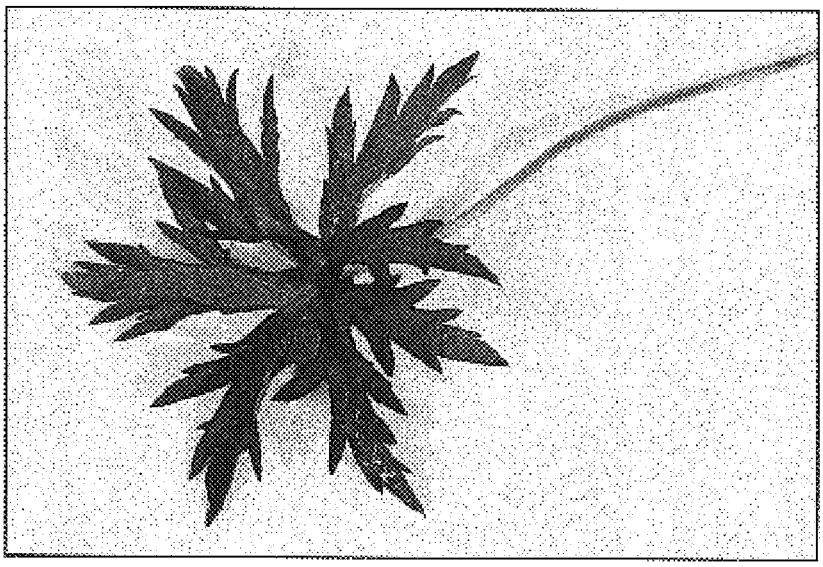

* * * * *